United States Patent [19]
Matsuo et al.

[11] Patent Number: 5,869,246
[45] Date of Patent: Feb. 9, 1999

[54] TRIPLEX OLIGONUCLEOTIDES TARGETED TO P120

[75] Inventors: Ken-ichi Matsuo; Yoshikazu Sugimoto; Norio Masuko; Yuji Yamada, all of Saitama, Japan

[73] Assignee: Taiho Pharmaceutical Co., Ltd., Tokyo, Japan

[21] Appl. No.: 666,420

[22] PCT Filed: Oct. 13, 1995

[86] PCT No.: PCT/JP95/02113

§ 371 Date: Jun. 12, 1996

§ 102(e) Date: Jun. 12, 1996

[87] PCT Pub. No.: WO96/11938

PCT Pub. Date: Apr. 25, 1996

[30] Foreign Application Priority Data

Oct. 14, 1994 [JP] Japan ..................................... 6-249467

[51] Int. Cl.⁶ .............................. C12Q 1/68; C12N 15/85; C07H 21/04
[52] U.S. Cl. ........................... 435/6; 435/91.31; 435/325; 435/366; 435/367; 536/23.1; 536/24.31; 536/24.33; 536/24.5
[58] Field of Search ................................... 536/24.5, 23.1, 536/24.3, 24.31, 24.33; 514/44; 435/375, 6, 325, 91.31, 366, 367

[56] References Cited

PUBLICATIONS

L. J. Maker III, et al. Bio Essays 14(12):807–815, '92.
Genesis Grap Associates, Inc., Abstract Acc. #01997756, Dialog IAC Newsletter OB, '96.
B. Tseng et al. Cancer Gene Therapy 1(1):65–71, '94.
J. Milligan et al. J. Med. Chem. 36(14):1923–1937, '93.
C. Stein et al. Science 261:1004–1012, '93.
R. Stull et al. Pharm. Res. 12(4):465–483, '95.
E. Uhlmann et al. Chem. Reviews 90(4) 543–584, '90.

*Primary Examiner*—John L. LeGuyader
*Attorney, Agent, or Firm*—Sughrue, Mion, Zinn, Macpeak & Seas, PLLC

[57] ABSTRACT

This invention provides a method for inhibiting transcription of a p120 gene, which comprises using an oligonucleotide capable of forming a triple-stranded chain in a homopurine/homopyrimidine region of the p120 gene, as well as an oligonucleotide capable of forming a triple-stranded chain, or a derivative thereof, which has the following nucleotide sequence GAAWGGAGGAGGAGAAA or a complementary sequence thereof, and a pharmaceutical composition which contains the oligonucleotide as its active ingredient and is useful as an agent for the prevention and treatment of cancers with less side effects.

6 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 17
        ( B ) TYPE: Nucleic Acid
        ( C ) STRANDEDNESS: Single
        ( D ) TOPOLOGY: Linear ( i i ) MOLECULE TYPE: Synthetic ( i i i ) HYPOTHETICAL: NO ( i v ) ANTI-SENSE: YES ( x i ) SEQUENCE DESCRIPTION: SEQ ID NO:1:

GAAWGGAGGA GGAGAAA      1 7

( 2 ) INFORMATION FOR SEQ ID NO:2:

( i ) SEQUENCE CHARACTERISTICS:
        ( A ) LENGTH: 17
        ( B ) TYPE: Nucleic Acid
        ( C ) STRANDEDNESS: Single
        ( D ) TOPOLOGY: Linear ( i i ) MOLECULE TYPE: Synthetic ( i i i ) HYPOTHETICAL: NO ( i v ) ANTI-SENSE: YES ( x i ) SEQUENCE DESCRIPTION: SEQ ID NO:2:

GAAAGGAGGA GGAGAAA      1 7

TRIPLEX OLIGONUCLEOTIDES TARGETED TO P120

This application is a 371 of PCT/JP95/02113, filed Oct. 13, 1995.

TECHNICAL FIELD

The present invention relates to an oligonucleotide or a derivative thereof which is useful in treating and preventing human cancers.

BACKGROUND ART

With the discovery of a number of cancer-related genes in recent years, revelation of the mechanism of malignant transformation has been slowly began. It has been shown that many cancers are certain genetic diseases caused by gene abnormalities. Since abnormal mutant cells originate naturally from normal cells, they are not easily recognized as foreign bodies in the living body, and their biological or biochemical properties are not so different, unlike the case of infectious diseases caused by the invasion of other organisms.

In consequence, though various anticancer drugs, therapeutic methods and reagents have been developed, they exert influences upon not only cancer cells but also normal tissues and normal cells because of their low selectivity for cancer cells, so that, in the present situation, the use of such drugs is strictly restricted due to their side effects no matter how they are effective.

On the contrary, controlling methods of the expression of specific genes have recently been developed making use of nucleic acids and their derivatives. Since cancers are genetic diseases as described above, cancer cell-specific effects can fully be expected by such expression controlling methods when a specific gene, particularly a malignant transformation factor, is used as the target.

One of such means is antisense method. In this method, a short oligonucleotide (approximately 15 to 30 base length) having a nucleotide sequence complimentary to a nucleotide sequence of a gene to be used as a target is introduced into cells to effect inhibition of transcription or translation of the malignant transformation gene. The antisense method is roughly divided into antigene method and antimessenger method depending on the target molecules.

The antimessenger method uses messenger RNA as the target. In this method, an oligonucleotide having a nucleotide sequence complementary to a target single-stranded RNA molecule is prepared to form a double-stranded chain by the Watson-Crick bonding, thus effecting inhibition of splicing or translation of the target RNA or its degradation with a double strand-specific RNA degrading enzyme. Unlike the case of the antigene method which will be described later, this method can use all RNA molecules as the target. Therefore, studies on this method have been reported using as the target various oncogenes such as c-myc gene (Nature, 328, 445–449, (1987)) and the like. However, since messenger RNA molecules are present in cells in a relatively large amount (especially in the case of malignant transformation factors), the amount of antisense molecules required for exerting influence upon cells also becomes large. Therefore, it is considered that even if its effect is recognized at the level of cultured cells, its clinical application is difficult for the present.

In the antigene method, on the contrary, an antisense molecule is wound round a double-stranded DNA chain of a target gene to form a triple-stranded chain. Because the amount of such target in cells is small, unlike the case of the antimessenger method whose target is messenger RNA, the antigene method which targets gene DNA seems to be a more suitable method for clinical application, when stability and the like of oligonucleotides in the living body are taken into consideration. Formation of the triple-stranded chain which is essential for the antigene method depends on the Hoogsteen bonding. It is known that one side of double-stranded DNA must have a continuous purine base sequence (homopurine/homopyrimidine sequence) for the formation of the Hoogsteen bonding.

Accordingly, the object of the present invention is to provide, making use of the antigene method, an oligonucleotide or a derivative thereof which acts selectively on cancer cells and is therefore useful as a pharmaceutical composition such as anticancer agent, a method for the prevention and treatment of cancers which uses the pharmaceutical composition, and a method for the inhibition of p120 gene transcription.

DISCLOSURE OF THE INVENTION

In view of the above, as a result of extensive investigation on the basis of a finding that a malignant transformation factor p120 does not exist in normal tissues in most cases but is present in various cancer tissues (Cancer Res., 48, 1244–1251 (1988)), the present inventors have found that growth of cancer cells can be inhibited selectively through specific inhibition of the expression of p120, and that since a homopurine/homopyrimidine region is present in the transcriptional control region of the gene DNA −1353/−1337 upstream of the translation initiation point, an antigene method in which a triple-stranded chain is formed by winding an antisense molecule or a sense molecule round this homopurine/homopyrimidine region can show more excellent effect in inhibiting expression of the gene than an antimessenger method which targets messenger RNA. The present invention has been completed based on these findings.

Thus, according to the present invention, there is provided an oligonucleotide or a derivative thereof, which has at least 15 continued bases of the nucleotide sequence shown in Sequence ID No. 1 and/or a complementary sequence of the nucleotide sequence, as well as a pharmaceutical composition which contains the oligonucleotide or a derivative thereof as an active ingredient, and a method for the prevention and treatment of cancers which comprises administering the pharmaceutical composition to mammals including human.

The present invention also provides a method for the inhibition of p120 gene transcription which comprises using an oligonucleotide capable of forming a triple-stranded chain in a homopurine/homopyrimidine region of the p120 gene. Since the transcription of the p120 gene is inhibited, this method is effective in inhibiting production of the p120 protein, thus exerting cancer cytotoxic activity.

The oligonucleotide of the present invention corresponds to the aforementioned homopurine/homopyrimidine region −1353/−1337 upstream of the p120 gene translation initiation point, and the −1340 position of the homopurine region is thymine which may be as such or replaced by adenine so that purine bases are continued. That is, W in Sequence ID No. 1 is thymine or adenine, and Sequence ID No. 2 is a homopurine sequence in which W is replaced by A. The oligonucleotide of the present invention also includes a homopyrimidine region sequence which is a complementary sequence of Sequence ID No. 1 (the complementary sequence of Sequence ID No. 2 is a homopyrimidine sequence). Each of the oligonucleotides of the Sequence ID No. 1 of the present invention and its complementary sequences becomes a sequence capable of forming a triple-stranded chain with the homopurine/homopyrimidine region when it has at least 15 continued bases.

The pharmaceutical composition of the present invention can contain each oligonucleotide of Sequence ID No. 1 in which W is T or A and complementary oligonucleotides thereof in the same composition alone or in combination thereof, and can be used by optionally adjusting formulation ratio of respective oligonucleotides.

The pharmaceutical composition of the present invention can be constructed from the aforementioned oligonucleotide and a known carrier for pharmaceutical use, and is useful especially as a drug for the prevention and treatment of cancers.

The oligonucleotide of the present invention can generally be synthesized using a commercially available DNA synthesizing apparatus in accordance with the known techniques. In that case, phosphodiester bonding may be replaced by methyl phosphate bonding (U.S. Pat. No. 4,511,713) or phosphorothioate bonding (JP-A-1-503302, the term "JP-A" as used herein means an "unexamined published Japanese patent application") in view of intracellular incorporation and stability. Each of these types can also be synthesized using a commercially available DNA synthesizing apparatus.

In addition, it is possible to improve affinity of an oligonucleotide containing this sequence for DNA by binding a DNA intercalater or the like to its 5'- or 3'-end or to increase its incorporation into cells by binding thereto a fat-soluble compound such as cholesterol. Acridine or a derivative thereof can be cited as an example of the DNA intercalater (WO 92/20698).

In consequence, examples of the oligonucleotide derivative of the present invention include those which have an effect to inhibit expression of p120 protein similar to the case of the inventive oligonucleotide, wherein the phosphodiester bonding is replaced by methyl phosphate bonding or phosphorothioate bonding or a DNA intercalater or a fat-soluble compound is linked to its 5'- or 3'-end.

Since the oligonucleotide of the present invention has strong effects to kill cells and inhibit expression of p120 protein, it can be used as an active ingredient of anticancer agents.

When the oligonucleotide of the present invention is applied as a medicine to mammals including human, it can be made into various dosage forms depending on each preventive or therapeutic purpose, such as oral preparations, injections, suppositories, preparations for external use (for example, cataplasmas, tapes and the like adhesive preparations, ointments, creams and lotions), eye drops, nasal drops and the like, and these preparations can be produced in accordance with respective medicine preparation techniques known to those skilled in the art.

When oral solid preparations are produced, the compound of the present invention is mixed with an excipient and, if necessary, a binder, a disintegrating agent, a lubricant, a coloring agent, a flavor, a smell corrigent and the like, and the resulting mixture is made into tablets, coated tablets, granules, powders, capsules and the like in an ordinary method. As such additives, various compounds generally used in this field can be used, for example, lactose, saccharose, sodium chloride, glucose, starch, calcium carbonate, kaolin, micro-crystalline cellulose, silicic acid and the like as excipients; water, ethanol, propanol, simple syrup, glucose solution, starch solution, gelatin solution, carboxymethylcellulose, hydroxypropylcellulose, hydroxypropylstarch, methylcellulose, ethylcellulose, shellac, calcium phosphate, polyvinyl pyrrolidone and the like as binders; dry starch, sodium alginate, agar powder, sodium hydrogencarbonate, calcium carbonate, sodium lauryl sulfate, stearic acid monoglyceride, lactose and the like as disintegrating agents; purified talc, stearic acid salt, borax, polyethylene glycol and the like as lubricants; and sucrose, bitter orange peel, citric acid, tartaric acid and the like as flavoring agents.

When oral liquid preparations are produced, the compound of the present invention is mixed with a flavoring agent, a buffer agent, a stabilizing agent, a smell corrigent and the like, and the resulting mixture is made into solutions for internal use, syrups, elixirs and the like in an ordinary method. In this case, the aforementioned flavoring agents may be used, sodium citrate and the like may be used as the buffer agent, and tragacanth, gum arabic, gelatin and the like may be used as the stabilizing agent.

When injections are produced, subcutaneous, intramuscular and intravenous injections can be prepared by mixing the compound of the present invention with a pH adjusting agent, a buffer agent, a stabilizing agent, an isotonic agent, a local anesthetic and the like in an ordinary method. Examples of the pH adjusting agent and buffer agent in this case include sodium citrate, sodium acetate, sodium phosphate and the like. As the stabilizing agent, sodium pyrosulfite, EDTA, thioglycolic acid, thiolactic acid and the like may be used. Examples of the local anesthetic include procaine hydrochloride, lidocaine hydrochloride and the like. Sodium chloride, glucose and the like may be used as the isotonic agent.

Suppositories can be produced by mixing the compound of the present invention with pharmaceutical carriers known in the art, such as polyethylene glycol, lanolin, cacao butter and fatty acid triglyceride, as well as Tween (trade name) and the like surfactants as occasion demands, and then shaping the resulting mixture in an ordinary method.

Ointments are produced by blending the compound of the present invention with generally used base materials, stabilizers, lubricant, preservatives and the like depending on each purpose, and mixing the formulation in an ordinary method. Examples of such base materials include liquid paraffin, white petrolatum, bleached beeswax, octyldodecyl alcohol, paraffin and the like. Examples of the preservatives include methyl paraoxybenzoate, ethyl paraoxybenzoate, propyl paraoxybenzoate and the like.

Adhesive preparations are produced in the usual way by coating a generally used support with the aforementioned ointments, creams, gels, pastes or the like. Examples of suitable support include woven or non-woven fabric made of cotton, staple fiber, chemical fiber and the like, and films or foam sheets of soft vinyl chloride, polyethylene, polyurethane and the like.

In addition, the compound of the present invention may be administered by encapsulating it into liposomes, in which the active ingredient is dispersed in fine particles composed of aqueous concentric layers adherent to fatty layers or used as a pharmacological composition to be included in other forms. Depending on its solubility, the effective compound may be present in both aqueous and fatty layers or used in the form of so-called liposome suspension. The hydrophobic layer consists of a phospholipid such as lecithin, a steroid such as cholesterol, a slightly ionic surfactant such as dicetyl phosphate, stearyl amine or phosphatidic acid, and/or other hydrophobic compounds. Particle size of liposomes is generally within the range of from about 15 nm to about 5 microns.

Though the content of the oligonucleotide of the present invention in pharmaceutical preparations varies depending on each preparation, it may preferably be within the range of approximately from 1 to 70% by weight in general.

Administration method of the pharmaceutical preparation of the present invention is not particularly limited and can be optionally decided depending on each dosage form, age, sex and other conditions of each patient, degree of symptoms and the like. For example, an injection preparation may be used for intravenous injection as such or by mixing it with usual auxiliary solutions such as of glucose, amino acids and the like, or it may be used alone for intraarterial, intramuscular, subcutaneous or intraperitoneal injection as occasion demands. Suppositories are administered into the rectum and ointments are applied to the skin, oral mucosa and the like.

Dose of the oligonucleotide of the present invention can be optionally selected depending on each administration method, age, sex and other conditions of each patient, degree of symptoms and the like. In general, the compound of the present invention may be administered in an approximate dose of from 0.01 to 1,000 mg/kg/day, preferably from 0.1 to 500 mg/kg/day. The daily dose recited above may be used once a day or divided into 2 to 4 daily doses.

BEST MODE OF CARRYING OUT THE INVENTION

The present invention is now illustrated in greater detail with reference to the following Inventive Example, Test Examples and Formulation Examples, but it should be understood that the present invention is not deemed to be limited thereto.

Inventive Example 1

Design and Production of Oligonucleotide

Figure 1:
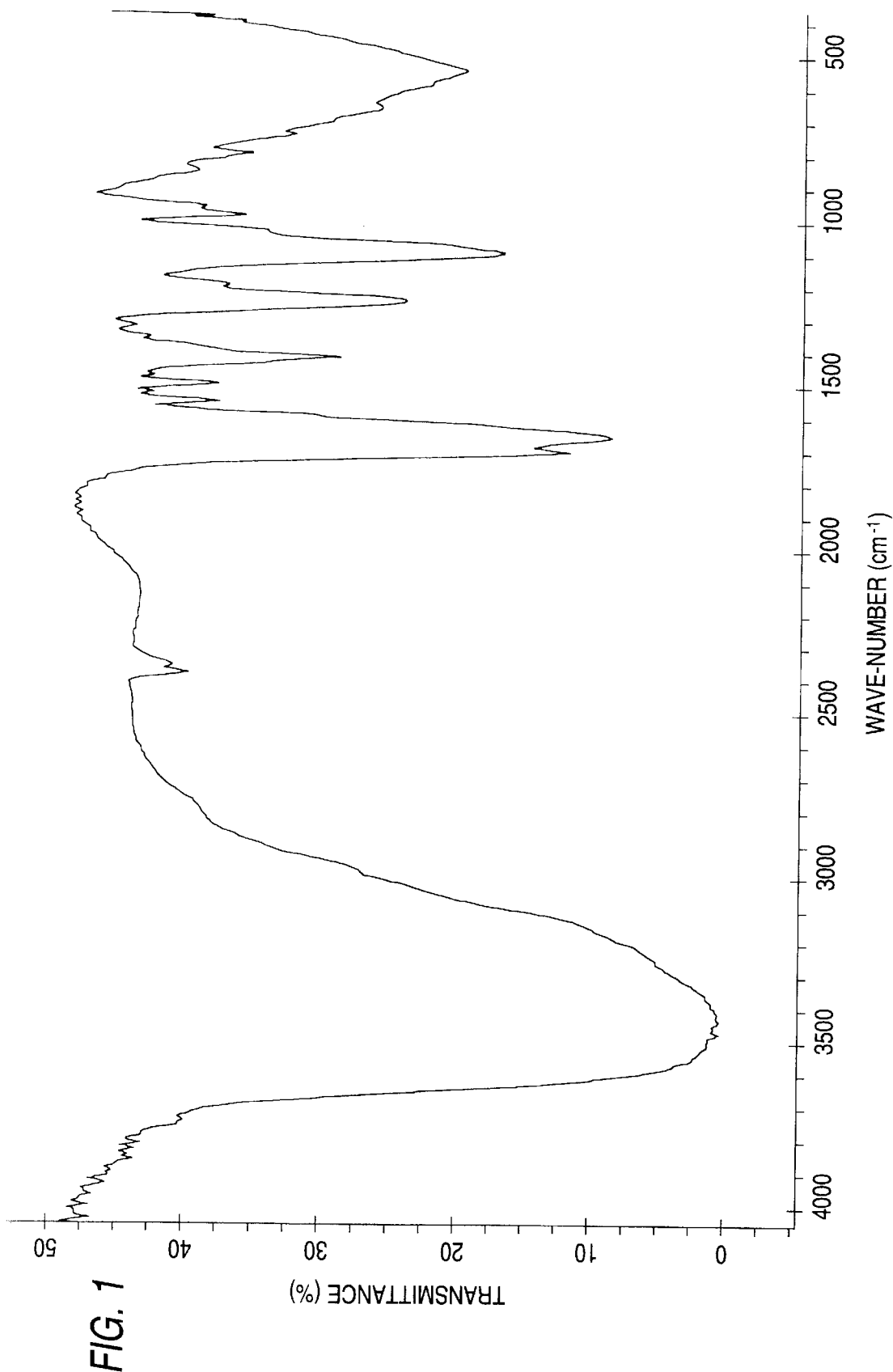
FIG. 1 is a graph showing infrared absorption spectrum of the oligonucleotide represented by Sequence ID No. 2.
Figure 2:
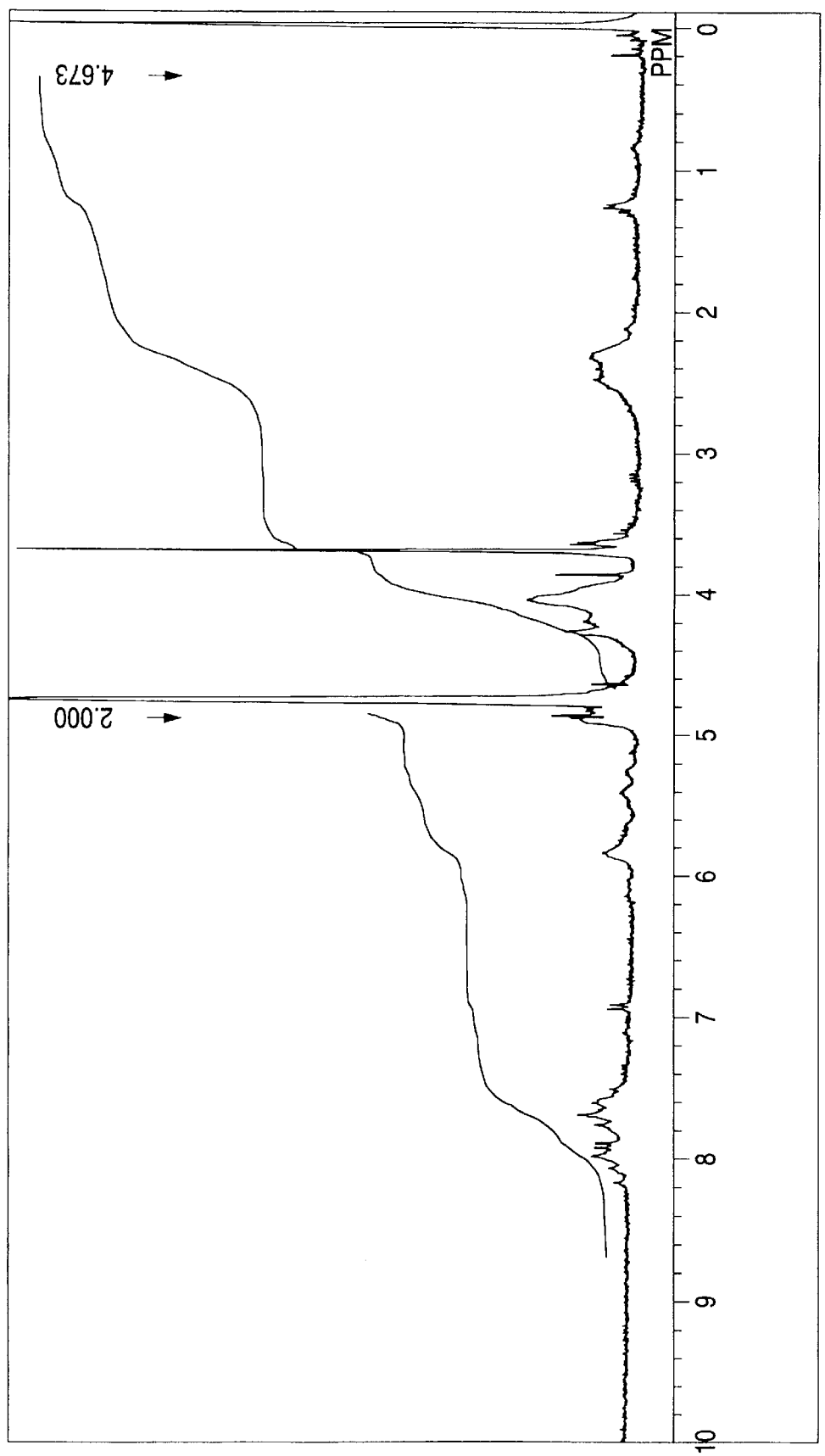
FIG. 2 is a graph showing nuclear magnetic resonance spectrum of the oligonucleotide represented by Sequence ID No. 2.

The homopurine/homopyrimidine sequence located in the upstream transcriptional control region of the p120 gene was selected as a triple-stranded chain forming sequence. In order to effect stable formation of the triple-stranded chain in cells, the antisense DNA sequence was made into an complementary sequence mostly consisting of homopurine. Based on the oligonucleotide designed in this way, the oligonucleotide shown in Sequence ID No. 2 was synthesized using a commercially available automatic DNA synthesizer (manufactured by Applied Biosystems) in which a β-cyanoethyl synthesis method was employed. A chart of infrared absorption spectrum (KBr method) is shown in FIG. 1, and a chart of nuclear magnetic resonance spectrum (in $D_2O$, 270 MHz) is shown in FIG. 2.

As control oligonucleotides of the antimessenger method, an antisense oligonucleotide (AACTTGCGCCCCATGGTA) and a sense oligonucleotide (TACCATGGGGCGCAAGTT), each consisting of 18 base pairs (-4 to +14) corresponding to the p120 translation codon (AUG site), were synthesized.

Test Example 1

Figure 3:
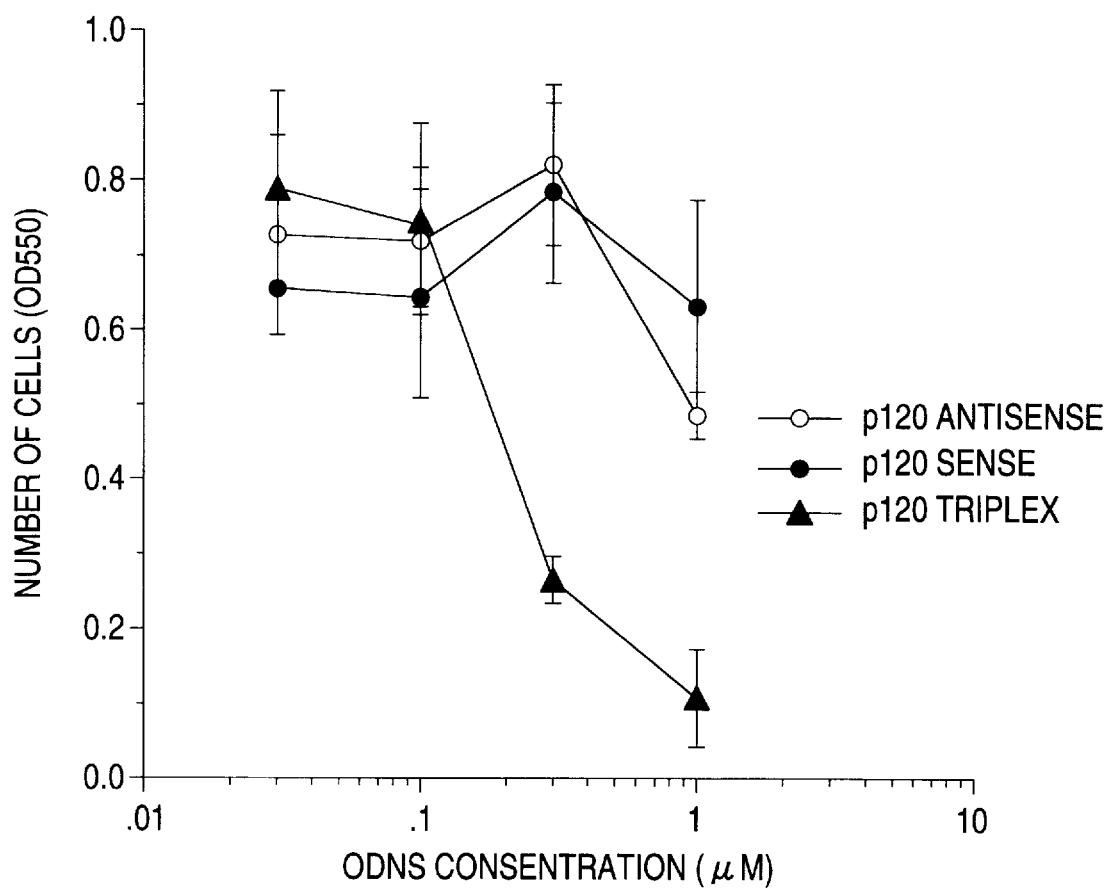
FIG. 3 is a graph showing Hela cytotoxic activities of the oligonucleotide of the present invention, and p120 sense and antisense oligonucleotides of antimessenger method.

Cytotoxic activity of the oligonucleotide obtained in Inventive Example 1 was examined using human cervical carcinoma HeLa cells in a cultured system. That is, $5 \times 10^2$ cells/100 μl/well of HeLa cells were seeded in a 96 well culture dish, and, after 2 days of culturing, each well was charged with 100 μl of a solution containing 4 μM of lipofectin and various amounts of each oligonucleotide, which have been allowed to react with each other at room temperature for 1 hour. After additional 3 days of culturing, the number of cells was determined by Crystal Violet method. The results are shown in FIG. 3. As is evident from the results, the DNA triple-stranded chain-forming oligonucleotide of the present invention (p120 triplex) shows distinctly strong cytotoxic activity in comparison with the antisense oligonucleotide (p120 antisense) and sense oligonucleotide (p120 sense) each consisting of 18 base pairs corresponding to the p120 translation codon.

Test Example 2

Figure 4:
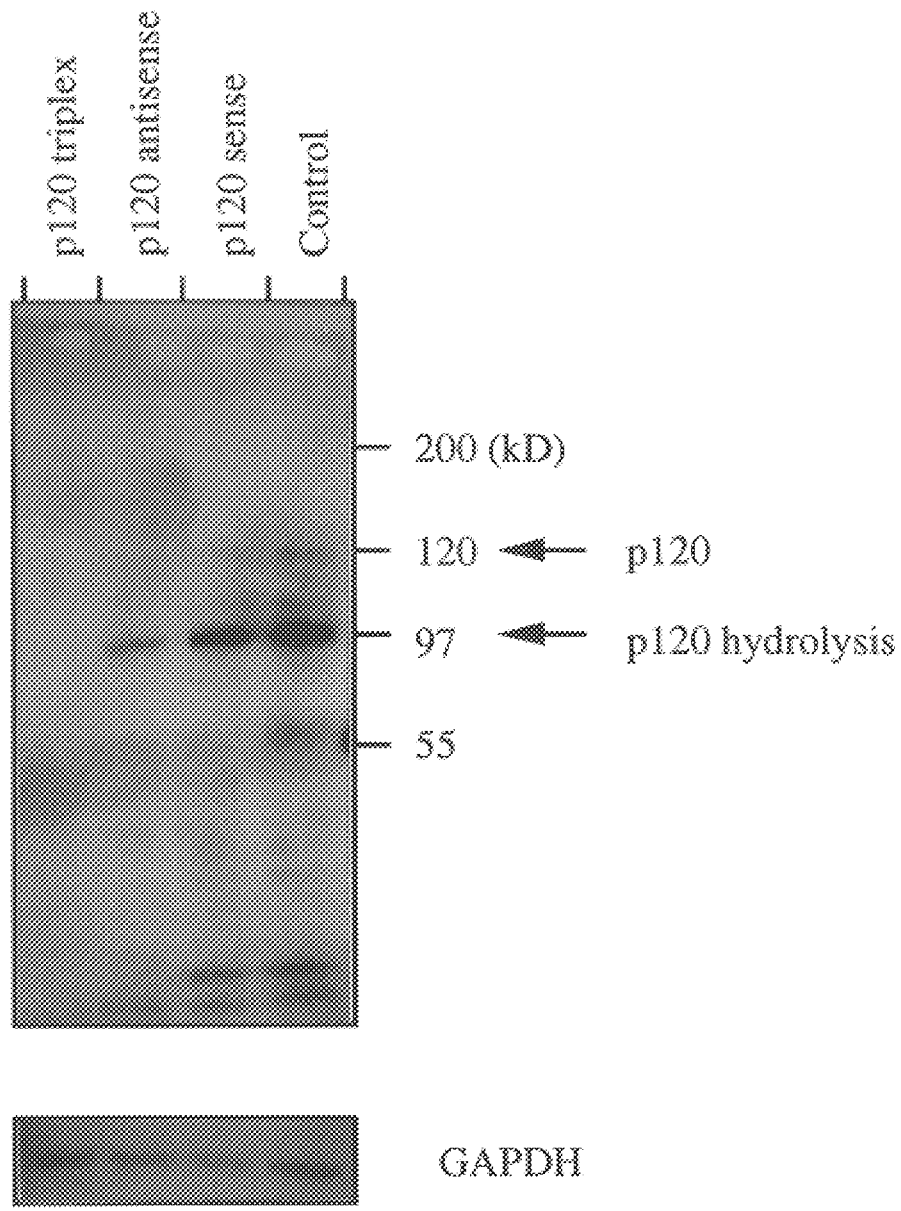
FIG. 4 is a graph showing effects of the oligonucleotide of the present invention, and p120 sense and antisense oligonucleotides of antimessenger method on the expression of p120 protein.

In order to confirm that the cytotoxic activity of the oligonucleotide of the present invention shown in Test Example 1 is caused by the inhibition of p120 expression, changes in the p120 protein were examined by Western blotting. That is, HeLa cells were cultured for 2 days in a 24 well plate, treated with the oligonucleotide in the same manner as described in Test Example 1 and cultured again for 7 days. Thereafter, the resulting cells were recovered by trypsin-EDTA treatment and then treated with a solubilizing agent (50 mM Tris buffer pH 7.5/0.05% SDS) to obtain a crude cell extract. After determination of protein concentration in each sample, a predetermined amount of the protein extract was subjected to SDS-PAGE electrophoresis. After the electrophoresis, protein was transferred onto a nitrocellulose membrane to determine the amount of p120 protein in each sample using an anti-p120 monoclonal antibody. As a control test, Western blotting was carried out in the same manner using GAPDH (glyceraldehyde phosphate dehydrogenase) which hardly changes by the condition of cell growth. As the results, expression of p120 protein was inhibited almost completely by the treatment with 0.5 μM of the oligonucleotide of the present invention (p120 triplex) as shown in FIG. 4. Since changes in the quantity of GAPDH expression are not detectable, it is considered that the oligonucleotide of the present invention causes exhaustion of p120 protein by selectively inhibiting transcription of the p120 gene, thereby resulting in the generation of the cytotoxicity shown in FIG. 3.

Formulation Example 1

Injection Preparation

| | |
|---|---|
| Inventive compound | 5 mg |
| distilled water for injection use | balance |
| per ampoule | 5 ml |

An injection preparation was prepared in an ordinary method using the above formulation.

Formulation Example 2

Capsule Preparation

| | |
|---|---|
| Inventive compound | 10 mg |
| Lactose | 50 mg |
| Corn starch | 47 mg |
| Crystalline cellulose | 50 mg |
| Talc | 2 mg |
| Magnesium stearate | 1 mg |
| per capsule | 160 mg |

A capsule preparation was prepared in an ordinary method using the above formulation.

Formulation Example 3

Suppository

| | |
|---|---|
| Inventive compound | 20 mg |
| Witepsol W-35 (trade name, manufactured by Dynamite Novel) | 1,380 mg |
| per one | 1,400 mg |

INDUSTRIAL APPLICABILITY

Since the oligonucleotide or a derivative thereof according to the present invention can inhibit transcription of the cancer-specific p120 gene broadly distributed in cancer cells, due to its property to form a triple-stranded chain, and as a result, inhibit expression of the p120 protein, it can inhibit growth of tumors and therefore is useful as an agent having low side effects for use in the prevention and treatment of cancers.

---

We claim:

1. An oligonucleotide or a derivative thereof comprising of at least 15 continuous bases of the nucleotide sequence of Sequence ID No. 1.

2. The oligonucleotide or a derivative thereof according to claim 1, wherein said oligonucleotide has 17 bases.

3. The oligonucleotide or a derivative thereof according to claim 1, wherein W is A.

4. The oligonucleotide or a derivative thereof according to claim 3, wherein said oligonucleotide has 17 bases.

5. An oligonucleotide or a derivative thereof comprising at least 15 continuous bases of a complementary sequence of the nucleotide sequence of Sequence ID No. 1.

6. A method for inhibiting transcription of a p120 gene, which comprises contacting an oligonucleotide with a double-stranded region of the p120 gene, wherein said region consists of a homopurine/homopyrimidine sequence, so as to form a triple-stranded chain.

* * * * *